United States Patent
Wang et al.

(10) Patent No.: US 10,037,742 B2
(45) Date of Patent: Jul. 31, 2018

(54) METHOD AND APPARATUS FOR DISPLAYING HEALTH DATA AND MEDIUM

(71) Applicant: Xiaomi Inc., Beijing (CN)

(72) Inventors: Chuan Wang, Beijing (CN); Yongfeng Xia, Beijing (CN); Pengfei Zhang, Beijing (CN); Heng Qu, Beijing (CN)

(73) Assignee: XIAOMI INC., Beijing (CN)

( * ) Notice: Subject to any disclaimer, the term of this patent is extended or adjusted under 35 U.S.C. 154(b) by 209 days.

(21) Appl. No.: 14/666,383

(22) Filed: Mar. 24, 2015

(65) Prior Publication Data

US 2016/0019858 A1 Jan. 21, 2016

Related U.S. Application Data

(63) Continuation of application No. PCT/CN2014/091737, filed on Nov. 20, 2014.

(30) Foreign Application Priority Data

Jul. 18, 2014 (CN) .......................... 2014 1 0344634

(51) Int. Cl.
*A61B 5/00* (2006.01)
*G06F 3/01* (2006.01)
(Continued)

(52) U.S. Cl.
CPC ............ *G09G 5/003* (2013.01); *A61B 5/0002* (2013.01); *G06F 3/017* (2013.01); *G09G 5/18* (2013.01);
(Continued)

(58) Field of Classification Search
CPC .................. A61B 5/0002; A61B 5/681; A61B 2560/0266; G06F 3/017; G09G 2370/16
See application file for complete search history.

(56) References Cited

U.S. PATENT DOCUMENTS 7,534,206 B1   5/2009  Lovitt et al.
7,605,714 B2  10/2009  Thompson et al.
(Continued)

FOREIGN PATENT DOCUMENTS

CN  202355405 U  8/2012
CN  202801577 U  3/2013
(Continued)

OTHER PUBLICATIONS

International Search Report dated Mar. 27, 2015 for International Application No. PCT/CN2014/091737, 4 pages.
(Continued)

*Primary Examiner* — Jacinta M Crawford
(74) *Attorney, Agent, or Firm* — Arch & Lake LLP

(57) ABSTRACT

The present disclosure relates to a method and an apparatus for displaying health data collected by a wearable device. The method may include acts performed by the wearable device: collecting health data of a user; establishing a wireless connection with a home media playing device; and sending the health data to the home media playing device through the wireless connection for display. The wearable device includes: a data collection module, a connection establishing module and a data sending module. By collecting health data of a user, establishing a wireless connection with a home media playing device, sending the health data to the home media playing device through the wireless connection, and displaying the health data by the home media playing device, the user operation is simplified, and the utilization efficiency is improved.

20 Claims, 10 Drawing Sheets

(51) Int. Cl.
*G09G 5/00* (2006.01)
*G09G 5/18* (2006.01)
*A61B 5/11* (2006.01)
*H04N 1/00* (2006.01)

(52) U.S. Cl.
CPC ............. *A61B 5/1122* (2013.01); *A61B 5/681* (2013.01); *A61B 5/742* (2013.01); *A61B 2560/0266* (2013.01); *A61B 2562/0219* (2013.01); *A61B 2562/08* (2013.01); *G09G 2370/16* (2013.01); *H04N 1/00381* (2013.01)

(56) References Cited

U.S. PATENT DOCUMENTS

| | | | |
|---|---|---|---|
| 8,562,489 B2* | 10/2013 | Burton | G04F 10/00 482/1 |
| 9,329,053 B2* | 5/2016 | Lakovic | G04F 10/00 |
| 9,696,811 B2* | 7/2017 | Yang | G06F 1/163 |
| 2004/0102683 A1* | 5/2004 | Khanuja | A61B 5/0002 600/300 |
| 2007/0281614 A1 | 12/2007 | Oliver et al. | |
| 2009/0121865 A1 | 5/2009 | Hamel et al. | |
| 2010/0048358 A1* | 2/2010 | Tchao | G06F 19/3418 482/9 |
| 2011/0125866 A1 | 5/2011 | Williams | |
| 2011/0283321 A1 | 11/2011 | Cruz et al. | |
| 2012/0218123 A1 | 8/2012 | Lusheng et al. | |
| 2012/0317511 A1 | 12/2012 | Bell | |
| 2013/0237193 A1* | 9/2013 | Dumas | G07C 9/00571 455/414.1 |
| 2013/0290427 A1 | 10/2013 | Proud | |
| 2014/0028546 A1* | 1/2014 | Jeon | G06F 3/014 345/156 |
| 2014/0089514 A1 | 3/2014 | Messenger et al. | |
| 2014/0135592 A1* | 5/2014 | Ohnemus | A61B 5/7275 600/301 |
| 2014/0320387 A1* | 10/2014 | Eriksson | G06F 3/017 345/156 |
| 2015/0022438 A1* | 1/2015 | Hong | H04M 1/7253 345/156 |
| 2015/0081763 A1* | 3/2015 | Sipola | A61B 5/00 709/203 |
| 2015/0185837 A1* | 7/2015 | Whitney | G06F 3/014 345/156 |
| 2015/0269825 A1* | 9/2015 | Tran | G08B 21/0446 340/539.12 |

FOREIGN PATENT DOCUMENTS

| | | |
|---|---|---|
| CN | 103393416 A | 11/2013 |
| CN | 10358484 A | 2/2014 |
| CN | 103876711 A | 6/2014 |
| CN | 103926890 A | 7/2014 |
| CN | 203693601 U | 7/2014 |
| CN | 104156186 A | 11/2014 |
| JP | 2008047022 A | 2/2008 |
| JP | 2010194140 A | 9/2010 |
| JP | 2011-039579 A | 2/2011 |
| JP | 2012020134 A | 2/2012 |
| JP | 2014041470 A | 3/2014 |
| RU | 2454924 C2 | 7/2012 |
| WO | WO 2006104480 A1 | 10/2006 |

OTHER PUBLICATIONS

Extended European Search Report for Application No. 15177550.9 dated Jan. 28, 2016.
International Search Report for international application No. PCT/CN2014/091737 dated Mar. 27, 2015.
Office Action for Japanese application No. 2016-533814 dated Oct. 4, 2016.
Office Action for Korean application No. 050240857 dated Jul. 12, 2016.
Office Action for Russian application No. 2015105277 dated Jul. 6, 2016.
Office Action for Chinese application No. 201410344634.9 dated Nov. 2, 2016.

* cited by examiner

|  | The received health data | The historical health data | | | |
|---|---|---|---|---|---|
|  | July 10, 2014 | July 9, 2014 | July 8, 2014 | July 7, 2014 | July 7, 2014 |
| Heart rate(Times/minutes) | 65 | 67 | 75 | 77 | 72 |
| Pulse rate(Times/minutes) | 71 | 72 | 75 | 79 | 80 |
| Respiratory frequency(Times/minutes) | 17 | 19 | 22 | 23 | 23 |
| Body temperature (Degree centigrade) | 37.0 | 37.2 | 37.0 | 36.8 | 36.5 |
| Blood pressure (millimeter of mercury) | 71/ 100 | 75/ 98 | 80/ 110 | 82/ 100 | 69/ 96 |
| Blood glucose(Mg/dl ) | 75 | 77 | 96 | 100 | 108 |
| Blood oxygen(Percent) | 92% | 95% | 93% | 95% | 90% |

METHOD AND APPARATUS FOR DISPLAYING HEALTH DATA AND MEDIUM

The present application is a continuation-in-part of International Application No. PCT/CN2014/091737, filed on Nov. 20, 2014, which is based upon and claims priority to Chinese Patent Application No. 201410344634.9, filed on Jul. 18, 2014, the entire contents of which are incorporated herein by reference.

TECHNICAL FIELD

The present disclosure relates to a field of data display, and more particularly to a method and an apparatus for displaying health data.

BACKGROUND

A wearable device (such as a smart bracelet, a smart watch and the like) is emerging electronic equipment at present, and mostly used to collect health data of a user.

Since most of the wearable devices have no display screen, in the related art, the wearable device needs to use a USB (Universal Serial Bus) data cable to connect with a computer, and then the health data in the wearable device are read and displayed through a supporting application program in the computer.

In the process of implementing the present disclosure, it is found that at least the following problems existing in the above manner: in the above displaying approach, the health data in a wearable device is displayed only after the wearable device and a computer are connected via a data cable by the user, whereby the operation process is complicated and the utilization efficiency is lower.

SUMMARY

In order to overcome the problems that in the related art the health data in a wearable device is displayed only after the wearable device and a computer are connected via a data cable, whereby the operation process is complicated and the utilization efficiency is lower, the present disclosure provides a method and an apparatus for displaying health data. The technical solutions are put forward as follows:

According to a first aspect of embodiments of the present disclosure, there is provided a method for displaying health data, used at a wearable device, the method includes: collecting health data of a user; establishing a wireless connection with a home media playing device; and sending the health data to the home media playing device through the wireless connection, the home media playing device being used to receive and display the health data.

According to a second aspect of the embodiments of the present disclosure, there is provided a method for displaying health data, used at a home media playing device, the method includes: establishing a wireless connection with the wearable device; receiving health data of a user sent by the wearable device through the wireless connection; and displaying the health data.

According to a third aspect of the embodiments of the present disclosure, there is provided an apparatus for displaying health data. The apparatus includes a processor and a memory for storing instructions executable by the processor. The processor is configured to: collect health data of a user; establish a wireless connection with a home media playing device; and send the health data to the home media playing device through the wireless connection, the home media playing device being used to receive and display the health data.

According to a fourth aspect of the embodiments of the present disclosure, there is provided an apparatus for displaying health data. The apparatus includes a processor; and a memory for storing instructions executable by the processor. The processor is configured to: establish a wireless connection with the wearable device; receive health data of a user sent by the wearable device through the wireless connection; and display the health data.

According to a fifth aspect of the embodiments of the present disclosure, there is provided a non-transitory readable storage medium including instructions executable by one or more processors in a terminal. The instructions cause the one or more processors to: collect health data of a user; establish a wireless connection with a home media playing device; and send the health data to the home media playing device through the wireless connection, the home media playing device being used to receive and display the health data.

According to a sixth aspect of the embodiments of the present disclosure, there is provided a non-transitory readable storage medium including instructions executable by one or more processors in a terminal. The instructions cause the one or more processors to: establish a wireless connection with the wearable device; receive health data of a user sent by the wearable device through the wireless connection; and display the health data.

It is to be understood that both the foregoing general description and the following detailed description are exemplary and explanatory only and are not restrictive of the present disclosure.

BRIEF DESCRIPTION OF THE DRAWINGS

The accompanying drawings, which are incorporated in and constitute a part of this specification, illustrate embodiments consistent with the invention and, together with the description, serve to explain the principles of the invention.

Explicit embodiments of the present disclosure that have been illustrated in the above accompany drawings will be described in more detail hereinafter. These accompany drawings and literal description are by no means intended to limit the scope of the idea of the present disclosure, but to explain the concept of the present disclosure to those skilled in the art with reference to particular embodiments.

DESCRIPTION OF THE EMBODIMENTS

Reference will now be made in detail to exemplary embodiments, examples of which are illustrated in the accompanying drawings. The following description refers to the accompanying drawings in which the same numbers in different drawings represent the same or similar elements unless otherwise represented. The implementations set forth in the following description of exemplary embodiments do not represent all implementations consistent with the invention. Instead, they are merely examples of apparatus and methods consistent with aspects related to the invention as recited in the appended claims.

The technical solutions provided by the embodiments of the present disclosure may include the following advantageous effects:

By collecting health data of a user, establishing a wireless connection with a home media playing device, sending the health data to the home media playing device through the wireless connection, and displaying the health data by the home media playing device, the disclosure solves problems regarding that the health data in a wearable device are displayed only after the wearable device and a computer are connected using a data cable. The wearable device may simplify the operation process and improve the utilization efficiency of the wearable device. Therefore, potential users are more willing to wear the wearable device and check their progress using the home media playing device with simplified operation and improved utilization efficiency.

Figure 1:
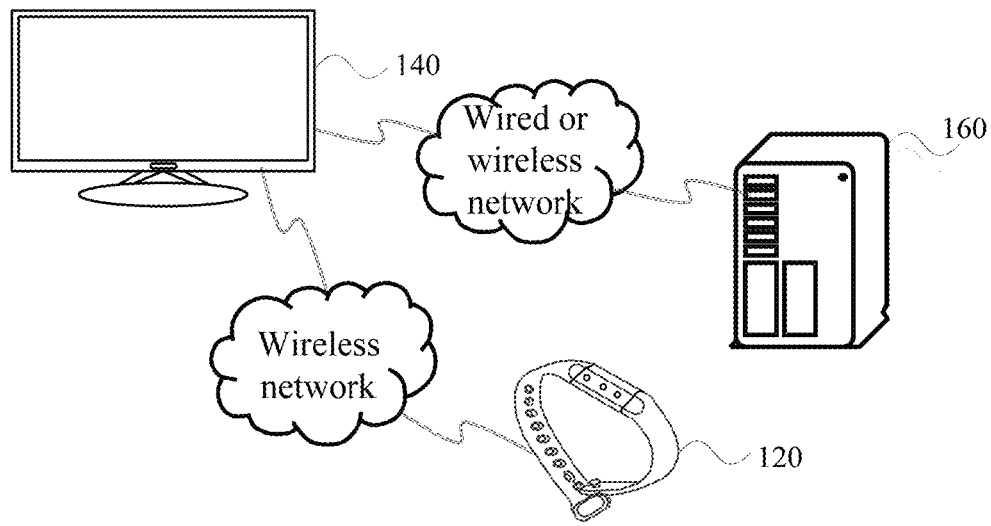
FIG. 1 is a structurally schematic diagram of an implementation environment involved in a method for displaying health data provided by embodiments of the present disclosure.

Referring to FIG. 1, it shows a structurally schematic diagram of an implementation environment involved in a method for displaying health data provided by each embodiment of the present disclosure. The implementation environment includes: a wearable device 120, a home media playing device 140 and a server 160. The wearable device 120 and the home media playing device 140 are connected with each other, the home media playing device 140 and the server 160 are connected with each other, and the wearable device 120 and the server 160 may also be connected with each other (not shown in FIG. 1).

The wearable device 120 may include a plurality of hardware sensors configured to collect data and communication circuits configured to transmit the collected data. For example, the wearable device 120 may be an electronic equipment having a function of collecting health data, and the electronic equipment may be a smart bracelet, a smart watch, and the like. The wearable device 120 may be attached to a user's body part such as a finger, a wrist, or other body parts. Thus, when the user moves the body part, the wearable device 120 may move consistently with the body part.

The wearable device 120 and the home media playing device 140 are connected with each other through a wireless network. The connection through the wireless network may include but is not limited to: WIFI (Wireless Fidelity) connection, Bluetooth connection or infrared connection.

The home media playing device 140 may be an electronic equipment including a display screen configured to display information. For example, the home media playing device 140 may be an electronic equipment having a function of receiving and displaying the health data, the electronic equipment may be a projector, a smart TV, or LCD (Liquid Crystal Display).

The home media playing device 140 and the server 160 are connected with each other through a wired or wireless network.

The server 160 may be a server, or a server cluster composed of several servers, or a cloud computing service center. The server 160 is a server, which may receive the health data uploaded by the home media playing device 140 and provide its historical uploaded health data to the home media playing device 140.

Figure 2:
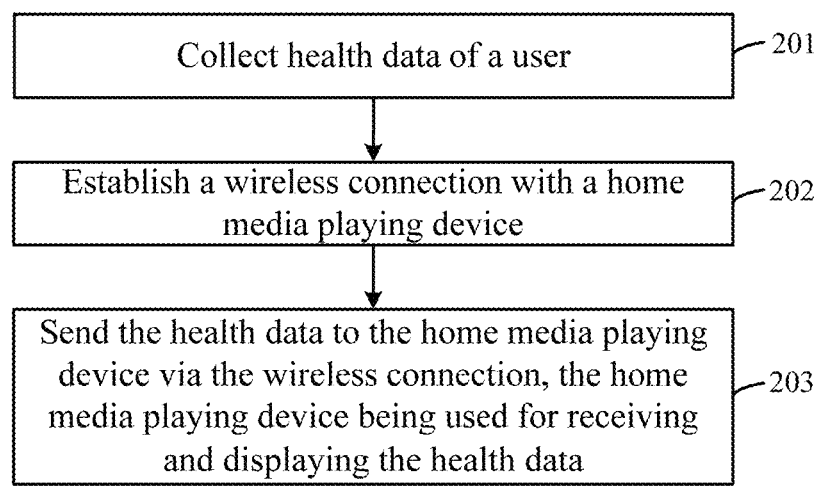
FIG. 2 is a flow chart showing a method for displaying health data according to embodiments of the disclosure.

Referring to FIG. 2, it shows a flow chart showing a method for displaying health data according to an exemplary embodiment. In the present embodiment, taking the method for displaying health data applied to the wearable device 120 shown in FIG. 1 as an example to illustrate. Referring to FIG. 2, the example flow chart of the method includes the following steps performed by a wearable device.

In step 201, health data of a user is collected. The user may be a human being, a pet, or any object of interest. The wearable device 120 may collect the data automatically when the wearable device is attached to a user. The health data may include but not limited to: daily steps, heart rate, pulse rate, respiratory frequency, body temperature, blood pressure, blood glucose, blood oxygen, body fat content, etc.

In step 202, a wireless connection with a home media playing device is established. The wireless connection may include WIFI connection, Bluetooth connection, or other connection standards.

In step 203, the health data is sent to the home media playing device through the wireless connection for display. For example, the home media playing device may be programmed to receive and display the health data.

In summary, the method for displaying health data provided by the embodiments of the present disclosure, by collecting health data of the user, establishing the wireless connection with the home media playing device, sending the health data to the home media playing device through the wireless connection, and displaying the health data by the home media playing device, the problems in the related that the health data in a wearable device is displayed only after the wearable device and a computer are connected using a data cable, the operation process is complicated and the utilization efficiency is lower are solved. Therefore, the user operation is simplified, and the utilization efficiency is improved.

Figure 3:
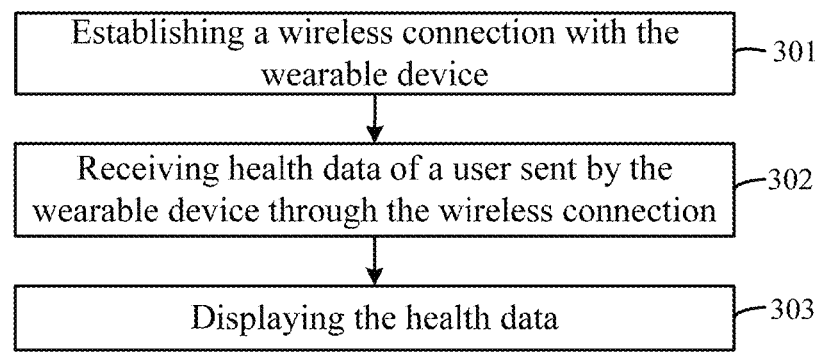
FIG. 3 is a flow chart showing a method for displaying health data according to embodiments of the disclosure.

Referring to FIG. 3, it shows a flow chart showing a method for displaying health data according to another exemplary embodiment. In the present embodiment, taking the method for displaying health data applied to the home media playing device 140 shown in FIG. 1 as an example to illustrate. Referring to FIG. 3, the example flow chart of the method includes the following steps.

In step 301, a wireless connection with the wearable device is established.

In step 302, health data of a user sent by the wearable device through the wireless connection is received.

In step 303, the health data is displayed. For example, the home media playing device may display health data collected in a preset time period. The preset time period may be adjusted directly using the wearable device by performing a gesture on the wearable device. The gesture may include tapping the wearable device, shaking the wearable device, or other body gestures involving the wearable device. The number of consecutive gestures may correspond to the duration of time to be included in the time period. For example, three consecutive tappings on the wearable device correspond to displaying health data in the last three days and four consecutive tappings on the wearable device correspond to displaying health data in the last four days. Alternatively or additionally, the preset time period may also be adjusted using the wearable device as a control input device to change the preset time period via a graphical user interface on the home media playing device.

In summary, the method for displaying health data provided by the embodiments of the present disclosure, by establishing the wireless connection with the wearable device, receiving health data of the user sent by the wearable device through the wireless connection; and displaying the health data, the problems in the related that the health data in a wearable device is displayed only after the wearable device and a computer are connected using a data cable, the operation process is complicated and the utilization efficiency is lower are solved. Therefore, the user operation is simplified, and the utilization efficiency is improved.

Figure 4A:
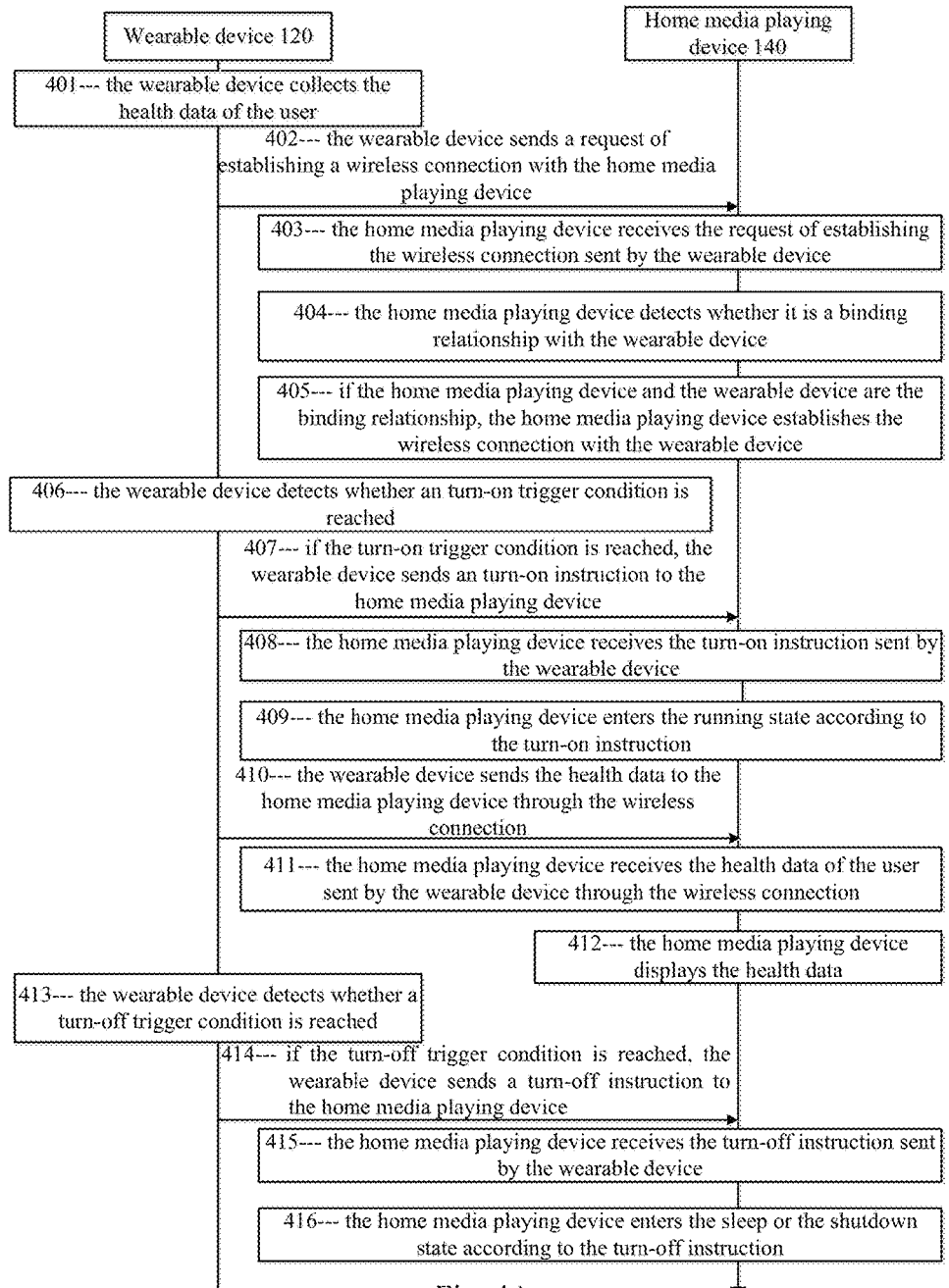
FIG. 4A is a flow chart showing a method for displaying health data according to embodiments of the disclosure.

Referring to FIG. 4A, it shows a flow chart showing a method for displaying health data according to a further exemplary embodiment. In the present embodiment, taking the method for displaying health data applied to the implementation environment shown in FIG. 1 as an example to illustrate. Referring to FIG. 4A, the example flow chart of the method includes the following steps.

In step 401, the wearable device collects health data of the user.

In the embodiments of the present disclosure, when the user wares the wearable device, the wearable device may collect health data of the user. That is, there are several sensors, such as a gravity accelerometer sensor, a pedometer, a heart rate sensor, a gyroscope sensor, an electronic compass sensor and the like, are set in the wearable device. The wearable device collects health data of the user by the sensor.

The health data including but not limited to: heart rate, pulse rate, respiratory frequency, body temperature, blood pressure, blood glucose, blood oxygen, body fat content, etc.

The wearable device carries a health data sensor, health data of the user is collected by the health data sensor. The health data sensor may include accelerometers, gyroscopes, motion sensors, humidity sensors, pulse sensors, microelectromechanical sensors, and other type of hardware sensors.

In step 402, the wearable device sends a request of establishing a wireless connection to the home media playing device.

When the wearable device needs to display the collected user's health data, the wearable device may send the request of establishing the wireless connection to the home media playing device. Optionally, the wearable device may add its own device identification in the request of establishing the wireless connection.

The wearable device may send the request of establishing the wireless connection to the home media playing device directly, and may also send the request of establishing the wireless connection to the home media playing device by a mobile terminal bound or paired with the wearable device. The mobile terminal that is bound or paired with the wearable device may be referred as the bound mobile terminal.

The wireless connection including but not limited to: WIFI connection, Bluetooth connection or infrared connection.

In step 403, the home media playing device receives the request of establishing the wireless connection sent by the wearable device.

The home media playing device may be a smart TV, the smart TV may receive the request of establishing the wireless connection sent by the wearable device.

In step 404, the home media playing device detects whether there is a binding relationship with the wearable device. The binding relationship may include a pairing relationship between two paired devices that can communicate using a wireless connection, which may include any connection under Bluetooth® or other standards.

The binding relationship may further represent the mutual trust relationship between the home media playing device and the wearable device.

When the home media playing device receives the request of establishing the wireless connection sent by the wearable device, the home media playing device detects whether the home media playing device and the wearable device are a binding relationship and determines whether the wireless connection is established with the wearable device according to a detection result.

Optionally, by comparing the device identification carried in the request of establishing the wireless connection and the device identification maintained by itself, the home media playing device may detect whether there is the binding relationship with the wearable device according to whether the identification carried in the request and the identification maintained by itself are the same.

In step 405, if the home media playing device and the wearable device are the binding relationship, the home media playing device establishes the wireless connection with the wearable device.

When the wearable device sends the request of establishing the wireless connection to the home media playing device directly, the home media playing device establishes the wireless connection with the wearable device directly; when the wearable device sends the request of establishing the wireless connection to the home media playing device by the mobile terminal bound with the wearable device, the home media playing device establishes the wireless connection with the wearable device by the mobile terminal bound with the wearable device.

Optionally, the home media playing device may send the response back to the wearable device after the wireless connection is established successfully, to represent that the wireless connection is established successfully.

In step 406, the wearable device detects whether a turn-on trigger condition exists.

When the wearable device receives the response sent back by the home media playing device, the wearable device detects whether the turn-on trigger condition exists.

The turn-on trigger condition may include but is not limited to: a first designated time is reached, or a collected body gesture conforms to a first gesture, or a distance between the wearable device and the home media playing device is less than a preset distance. The turn-on trigger condition occurs when any of the above condition is reached.

The first designated time may be determined according to the experience, and a determined principle thereof is subject to ensure that the wearable device may collect reliable health data. In general, when a user is on an empty stomach, the wearable device may collect comparatively reliable health data, therefore, the first designated time may be determined as 8 o'clock every morning, or the first designated time may also be determined as 7 o'clock every morning Optionally, the wearable device may detect whether the first designated time is reached by an application program representing the time carried by itself.

The first gesture may include a gesture which is able to interact with the wearable device, for example, the first gesture may include: a circle gesture of the wearable device, a cross gesture of the wearable device, or any preset gestures defined by the user with the wearable device.

Optionally, the wearable device may collect the user's body gesture through the gesture sensor carried by itself, and detect whether it conforms to the first gesture by comparing the collected body gesture and the body gesture maintained by itself.

The preset distance may be determined according to the experience, and a determined principle thereof is subject to ensure that reliable data communication may be made between the wearable device and the home media playing device.

Optionally, the wearable device may detect whether the distance between the wearable device and the home media playing device is less than the preset distance through a short distance wireless communication component carried by itself. For example, the wearable device may detect whether the distance between the wearable device and the home media playing device is less than the preset distance through a Bluetooth location; or the wearable device may also detect whether the distance between the wearable device and the home media playing device is less than the preset distance through an Infrared location.

Optionally, the wearable device may also detect whether the distance between the wearable device and the home media playing device is less than the preset distance through a short distance wireless communication technology supported by itself. For example, the wearable device detects whether the distance between the wearable device and the home media playing device is less than the preset distance through a WIFI communication technology.

When the wearable device detects that the time reaches the first designated time, or the body gesture collected by the wearable device conforms to the first gesture, or the wearable device detects whether the distance between the wearable device and the home media playing device is less than the preset distance, the wearable device detects that the turn-on trigger condition exists.

In step 407, if the turn-on trigger condition exists, the wearable device sends a turn-on instruction to the home media playing device.

When the wearable device detects that the turn-on trigger condition exists, the wearable device sends the turn-on instruction to the home media playing device, so that the home media playing device may enter an operating state according to the turn-on instruction.

Fox example, the smart bracelet sends the turn-on instruction to the smart TV at 8 o'clock every morning.

In step 408, the home media playing device receives the turn-on instruction sent by the wearable device.

After the wearable device sends the turn-on instruction to the home media playing device, the home media playing device receives the turn-on instruction.

In step 409, the home media playing device enters the operating state according to the turn-on instruction.

When the home media playing device receives the turn-on instruction sent by the wearable device, the home media playing device enters the operating state according to the turn-on instruction.

Optionally, when entering the operating state, the home media playing device may send the response back to the wearable device, to represent that the home media playing device itself has entered the operating state.

For example, the smart TV enters the operating state at 8 o'clock every morning according to the turn-on instruction sent by the wearable device.

In step 410, the wearable device sends the health data to the home media playing device through the wireless connection.

When the wearable device receives the response sent by the home media playing device, the wearable device sends the collected health data to the home media playing device through the wireless connection between the wearable device and the home media playing device.

In step 411, the home media playing device receives health data of the user sent by the wearable device through the wireless connection.

When the wearable device sends the collected health data to the home media playing device through the wireless connection between the wearable device and the home media playing device, the home media playing device receives the health data.

In step 412, the home media playing device displays the health data.

When the home media playing device receives the health data sent by the wearable device, the home media playing device displays the health data.

Optionally, when the health data is sent to the home media playing device, the wearable device may add a user account in the health data, so that when the home media playing device receives the health data, the home media playing device may acquire historical health parameter corresponding to the user account from the server according to the user account carried in the health data and display the historical health data while displaying the received health data.

Optionally, the home media playing device may integrate the received health data and the acquired historical health data, and then display them.

Figures 4B, 4C:
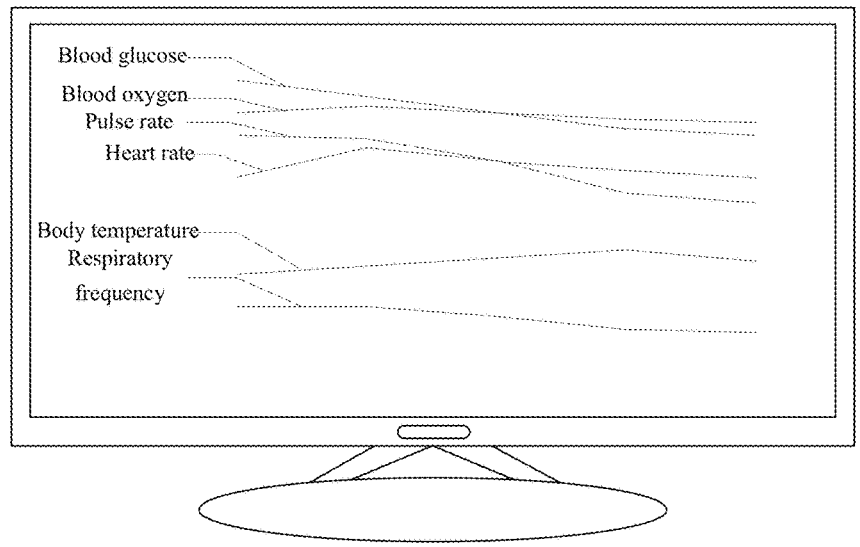
FIG. 4B is a schematic diagram of a health data display provided by an embodiment shown in FIG. 4A.
FIG. 4C is a schematic diagram of another health data display provided by an embodiment shown in FIG. 4A.

For example, the home media playing device may integrate the received health data and the acquired historical health data as a table form shown in FIG. 4B, so that a contrast relationship between the present received health data and the acquired historical health data is more obviously, and the user may understand their own health state more clearly according to the contrast relationship.

For another example, the home media playing device may integrate the received health data and the acquired historical health data as a graph form shown in FIG. 4C, so that the fluctuations of the present received health data and the acquired historical health data are displayed more intuitively, and the user may understand their own health state more intuitively according to the graph.

In step 413, the wearable device detects whether a turn-off trigger condition exists.

The turn-off trigger condition may include but is not limited to: a second designated time is reached, or a collected body gesture conforms to a second gesture, or a distance between the wearable device and the home media playing device is greater than a preset distance.

The second designated time may be determined according to the experience, and a determined principle thereof is subject to ensure that the user has consulted the health data displayed by the home media playing device.

Optionally, the wearable device may detect whether the first designated time is reached by an application program representing the time carried by itself The second gesture may include a gesture which is able to interact with the wearable device. For example, the second gesture may include: a gesture that the user draws horizontal line with the wearable device, or a gesture that the user draws vertical line with wearable device, or other preset gestures defined by the user with the wearable device.

Optionally, the wearable device may collect the user's body gesture through the gesture sensor carried by itself, and detect whether it conforms to the second gesture by comparing the collected body gesture and the body gesture maintained by itself.

The preset distance may be determined according to the experience, and a determined principle thereof is subject to ensure that reliable data communication may be made between the wearable device and the home media playing device.

Optionally, the wearable device may detect whether the distance between the wearable device and the home media playing device is greater than the preset distance through a short distance wireless communication component carried by itself. For example, the wearable device may detect whether the distance between the wearable device and the home media playing device is greater than the preset distance through a Bluetooth location; or the wearable device may also detect whether the distance between the wearable device and the home media playing device is greater than the preset distance through an Infrared location.

Optionally, the wearable device may also detect whether the distance between the wearable device and the home media playing device is greater than the preset distance through a short distance wireless communication technology supported by itself. For example, the wearable device detects whether the distance between the wearable device and the home media playing device is greater than the preset distance through a WIFI communication technology.

When the wearable device detects that the time reaches the second designated time, or the body gesture collected by the wearable device conforms to the second gesture, or the wearable device detects whether the distance between the wearable device and the home media playing device is greater than the preset distance, the wearable device detects that the turn-off trigger condition exists.

It should be noted that, the second gesture may be the same as the above first gesture, and may also be different from the above first gesture. When the second gesture is the same as the first gesture, if the current home media playing device is on a sleep or a shutdown state, the home media playing device enters the operating state after receiving the gesture; if the current home media playing device is on the sleep or the shutdown state, the home media playing device enters the sleep or the shutdown state after receiving the gesture.

In step 414, if the turn-off trigger condition exists, the wearable device sends a turn-off instruction to the home media playing device.

When the wearable device detects that the turn-off trigger condition exists, the wearable device sends the turn-off instruction to the home media playing device, so that the home media playing device may enter the sleep or the shutdown state according to the turn-off instruction.

In step 415, the home media playing device receives the turn-off instruction sent by the wearable device.

After the wearable device sends the turn-off instruction to the home media playing device, the home media playing device receives the turn-off instruction.

In step 416, the home media playing device enters the sleep or the shutdown state according to the turn-off instruction.

When the home media playing device receives the turn-off instruction sent by the wearable device, the home media playing device enters the sleep or the shutdown state according to the turn-off instruction.

In summary, the method for displaying health data provided by the embodiments of the present disclosure. The wearable device sends the request of establishing the wireless connection to the home media playing device when collecting health data of the user, the wearable device sends the health data to the home media playing device after the connection is established with the home media playing device, and the home media playing device displays the health data after receiving the health data sent by the wearable device. The wearable device solves the problems related to that the health data in a wearable device is displayed only after the wearable device and a computer are connected using a data cable. Thus, the wearable device makes the operation process less complicated and improves the utilization efficiency. Therefore, the user operation is simplified, and the utilization efficiency is improved.

The method for displaying health data provided by the embodiments of the present disclosure, the wearable device may add the user account in the health data when sending the health data to the home media playing device, the home media playing device uploads the health data to the server after receiving the health data, and acquires the historical health data corresponding to the user account from the server according to the user account carried by the health data, to integrate and display the health data and the historical health data, so that the user may understand their own health state more clearly and intuitively, and the integrity of the user's data saved by the server is ensured.

The method for displaying health data provided by the embodiments of the present disclosure, the home media playing device detects whether the home media playing device and the wearable device are a binding relationship after receiving the request of establishing the connection sent by the wearable device; if the home media playing device and the wearable device are the binding relationship, the wireless connection between the home media playing device and the wearable device is established, therefore, the security of establishing the wireless connection is ensured.

The method for displaying health data provided by the embodiments of the present disclosure, the wearable device sends the turn-on instruction to the home media playing device when detecting the turn-on trigger condition, so that the home media playing device enters the operating state according to the turn-on instruction, and receives the health data sent by the wearable device; therefore, it is ensured that the home media playing device may accurately receive the health data; further, the wearable device sends the turn-off instruction to the home media playing device when detecting the turn-off trigger condition, so that the home media playing device enters the sleep or the shutdown state according to the turn-off instruction; therefore, the security of health data of the user is ensured.

The method for displaying health data provided by the embodiments of the present disclosure, the wearable device sends the turn-on instruction to the home media playing device when detecting that the first designated time is reached, or detecting that the collected body gesture conforms to the first gesture, or detecting that the distance between the wearable device and the home media playing device is less than the preset distance, and sends the turn-off instruction to the home media playing device when detecting that the second designated time is reached, or detecting that the collected body gesture conforms to the second gesture, or detecting that the distance between the wearable device and the home media playing device is greater than the preset distance; therefore, a trigger mode of the trigger open condition and the closed condition is enriched.

In the above step 403 to step 405, the wearable device and the home media playing device need to be bound firstly before the wireless connection between the wearable device and the home media playing device is established.

In the embodiments of the present disclosure, the binding between the wearable device and the home media playing device includes the following three cases.

In the first case, the wearable device sends a wearable device identification and a user account to a server, while the home media playing device also sends an identification of the home media playing device and a user account to the server, and the binding to the wearable device, the home media playing device and the user account may be made by the server according to the identification of the wearable device, the identification of the home media playing device and the user account.

In the second case, the wearable device sends the identification of the wearable device and the user account to the server by a bound mobile terminal, while the home media playing device also sends the identification of the home media playing device and the user account to the server, the binding to the wearable device, the home media playing device and the user account may be made by the server according to the identification of the wearable device, the identification of the home media playing device and the user account.

In the third case, the wearable device sends the identification of the wearable device and the user account to the server by the home media playing device, while the home media playing device also sends the identification of the home media playing device and the user account to the server, the binding to the wearable device, the home media playing device and the user account may be made by the server according to the identification of the wearable device, the identification of the home media playing device and the user account.

In the above three cases, the identification of the wearable device is used to uniquely identify a wearable device, the identification of the home media playing device is used to uniquely identify a home media playing device, the user account to the server sent by the wearable device and the user account to the server sent by the home media playing device may be the same or different. Hereinafter, the above three cases will be briefly described in conjunction with the form of the accompanying drawings.

Figure 4D:
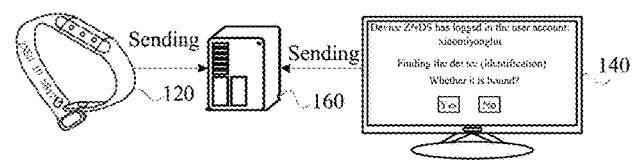
FIG. 4D is a schematic diagram of a binding relationship between a wearable device and a home media playing device is established provided by an embodiment shown in FIG. 4A.

Referring to FIG. 4D, it shows a schematic diagram of a binding relationship between a wearable device and a home media playing device is established provided by an embodiment shown in FIG. 4A. In a simple example shown in the FIG. 4D, the identification of the home media playing device is: ZNDS, its user account is: xiaomiyonghu, the identification of the wearable device is: 'ZNSH ID 5847', the wearable device 120 sends its own device identification is 'ZNSH ID 5847' to the server 160, meanwhile, the home media playing device 140 sends its own device identification ZNDS and its own user account 'xiaomiyonghu' logged in to the server 160, the server 160 may make a binding to the wearable device 120, the home media playing device 140 and the user account after receiving the identification of the wearable device, the identification of the home media playing device and the user account of the home media playing device. The server 160 may display the information on the wearable device 120, the home media playing device 140 and the user account on the display screen of the home media playing device 140 for the user to view and bind them according to the user's operation. As shown in FIG. 4D, when the user selects "yes" shown on the home media playing device 140, the server 160 performs the operation of binding the wearable device 120, the home media playing device 140 and the user account 'xiaomiyonghu'.

Figure 4E:
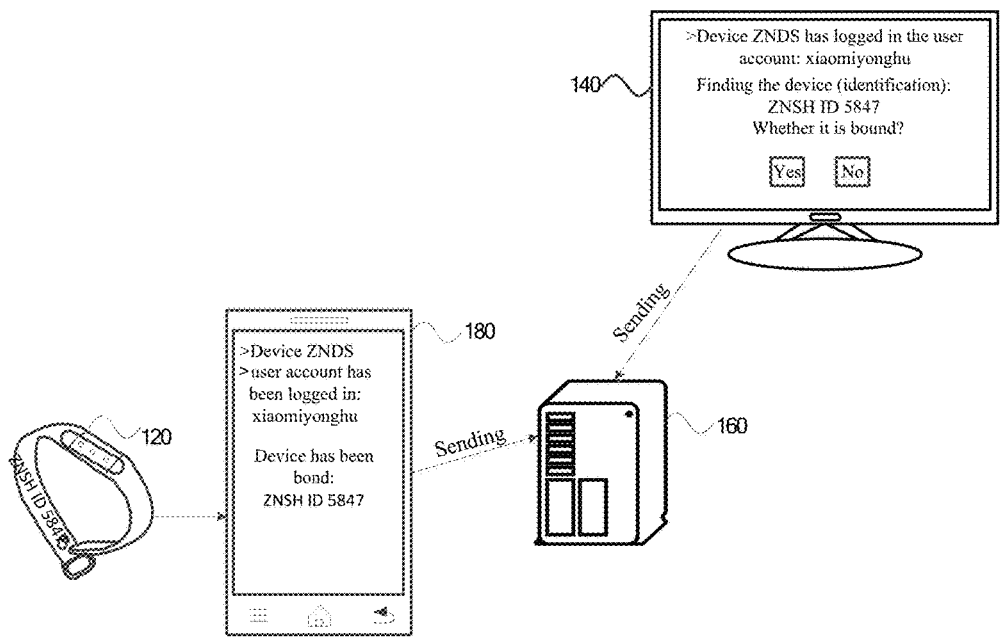
FIG. 4E is a schematic diagram of another binding relationship between a wearable device and a home media playing device is established provided by an embodiment shown in FIG. 4A.

Referring to FIG. 4E, it shows a schematic diagram of another binding relationship between a wearable device and a home media playing device is established provided by an embodiment shown in FIG. 4A. In a simple example shown in the FIG. 4E, the identification of the home media playing device is: ZNDS, its user account is: xiaomiyonghu, the identification of the wearable device is: 'ZNSH ID 5847', the wearable device 120 has established the binding relationship with the mobile terminal 180 in advance, the specific binding process is the same or similar with that shown in FIG. 4D, therefore, will not repeat here. The wearable device 120 may send its own device identification 'ZNSH ID 5847' to the server 160 by mobile terminal 180. In one possible implementation way, the wearable device 120 sends its own device identification 'ZNSH ID 5847' to the server 160 firstly, and then the mobile terminal 180 sends the identification of the wearable device 'ZNSH ID 5847' to the server 160. In another possible implementation way, the wearable device 120 may only send the instruction to the mobile terminal 180 and inform the mobile terminal 180 to send the identification of the wearable device to the server 160, and then the mobile terminal 180 sends the identification of the wearable device 'ZNSH ID 5847' saved by itself to the server 160. At the same time when the wearable device 120 sends the identification of the wearable device to the server 160 by the mobile terminal 180, the home media playing device 140 sends its own device identification ZNDS and its own user account 'xiaomiyonghu' logged in to the server 160. The server 160 may make a binding to the wearable device 120, the home media playing device 140 and the user account 'xiaomiyonghu' after receiving the identification of the wearable device, the identification of the home media playing device and the user account of the home media playing device. The server 160 may display the information of the wearable device 120, the home media playing device 140 and the user account on the display screen of the home media playing device 140 for the user to view and bind them according to the user's operation. As shown in FIG. 4E, when the user selects "yes" shown on the home media playing device 140, the server 160 performs the operation of binding the wearable device 120, the home media playing device 140 and the user account 'xiaomiyonghu'.

Figure 4F:
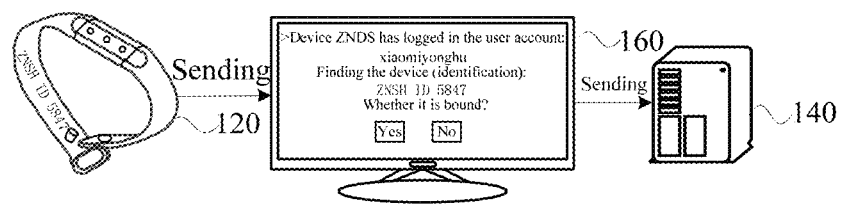
FIG. 4F is a schematic diagram of a further binding relationship between a wearable device and a home media playing device is established provided by an embodiment shown in FIG. 4A.

Referring to FIG. 4F, it shows a schematic diagram of a further binding relationship between a wearable device and a home media playing device is established provided by an embodiment shown in FIG. 4A. In a simple example shown in the FIG. 4F, the identification of the home media playing device is: ZNDS, its user account is: xiaomiyonghu, the identification of the wearable device is: 'ZNSH ID 5847', the wearable device 120 may send its own device identification 'ZNSH ID 5847' to the server 160 by the home media playing device 140. In one possible implementation way, the wearable device 120 sends its own device identification 'ZNSH ID 5847' to the server 160 firstly, and then the home media playing device 140 sends the identification of the wearable device 'ZNSH ID 5847' to the server 160. At the same time when the wearable device 120 sends the identification of the wearable device to the server 160 by the home media playing device 140, the home media playing device 140 sends its own device identification ZNDS and its own user account 'xiaomiyonghu' logged in to the server 160. The server 160 may make a binding to the wearable device 120, the home media playing device 140 and the user account 'xiaomiyonghu' after receiving the identification of the wearable device, the identification of the home media playing device and the user account of the home media playing device. The server 160 may display the information of three on the display screen of the home media playing device 140 for the user to view and bind them according to the user's operation. As shown in FIG. 4F, when the user selects "yes" shown on the home media playing device 140, the server 160 performs the operation of binding the wearable device 120, the home media playing device 140 and the user account 'xiaomiyonghu'.

In summary, in the method for displaying health data provided by the embodiments of the present disclosure, by establishing the binding relationship between the wearable device and the home media playing device in advance, it is ensured that the method for displaying the healthy data may be carried out smoothly; further, by sending the identification of the wearable device, the identification of the home media playing device and the user account to the server, or sending the identification of the wearable device, the identification of the home media playing device and the user account to the server by the bound mobile terminal, or sending the identification of the wearable device, the identification of the home media playing device and the user account to the server by the home media playing device, the binding among the wearable device, the home media playing device and the user account may be made by the server, the variety of the binding way is ensured.

The followings are apparatus embodiments of the present disclosure, which can be used to perform the method embodiments of the present disclosure. As for the details do not disclosed in the apparatus embodiments of the present disclosure, please refer to the method embodiments of the present disclosure.

Figure 5:
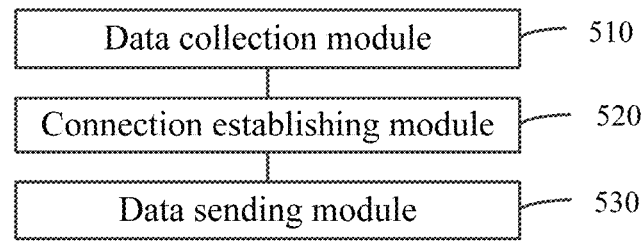
FIG. 5 is a block diagram of an apparatus for displaying health data according to embodiments of the disclosure.

Referring to FIG. 5, it shows a block diagram of an apparatus for displaying health data according to an exemplary embodiment. The apparatus for displaying health data may be implemented as a part of the wearable device 120 or the entire wearable device 120 in the implementation environment shown in FIG. 1 through software, hardware, or combination thereof. The file execution apparatus may comprise: a data collection module 510, a connection establishing module 520 and a data sending module 530.

The data collection module 510 is configured to collect health data of a user.

The connection establishing module 520 is configured to establish a wireless connection with a home media playing device.

The data sending module 530 is configured to send the health data to the home media playing device through the wireless connection, where the home media playing device is programmed to receive and display the health data.

In summary, in the apparatus for displaying health data provided by the embodiments of the present disclosure, by collecting health data of the user, establishing the wireless connection with the home media playing device, sending the health data to the home media playing device through the wireless connection, and displaying the health data by the home media playing device, the problems in the related that the health data in a wearable device is displayed only after the wearable device and a computer are connected using a data cable, causing that the operation process is complicated and the utilization efficiency is lower, may be solved. Therefore, the user operation is simplified, and the utilization efficiency is improved.

Figure 6:
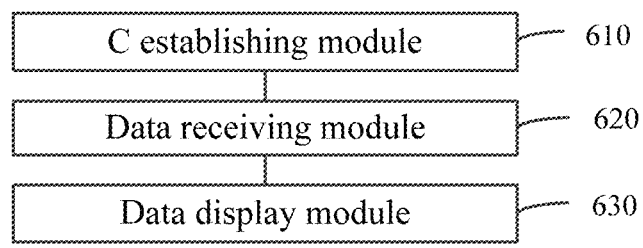
FIG. 6 is a block diagram of an apparatus for displaying health data according to embodiments of the disclosure.

Referring to FIG. 6, it shows an example block diagram of an apparatus for displaying health data according to another exemplary embodiment. The apparatus for displaying health data may be implemented as a part or all of the home media playing device 140 in the implementation environment shown in FIG. 1 through software, hardware, or combination thereof. The file execution apparatus may comprise: a connection establishing module 610, a data receiving module 620 and a data display module 630.

The connection establishing module 610 is configured to establish a wireless connection with the wearable device.

The data receiving module 620 is configured to receive health data of a user sent by the wearable device through the wireless connection.

The data display module 630 is configured to display the health data.

In summary, in the apparatus for displaying health data provided by the embodiments of the present disclosure, by establishing the wireless connection with the wearable device, receiving health data of the user sent by the wearable device through the wireless connection; and displaying the health data, the problems in the related that the health data in a wearable device is displayed only after the wearable device and a computer are connected using a data cable, causing that the operation process is complicated and the utilization efficiency is lower are solved. Therefore, the user operation is simplified, and the utilization efficiency is improved.

Figure 7:
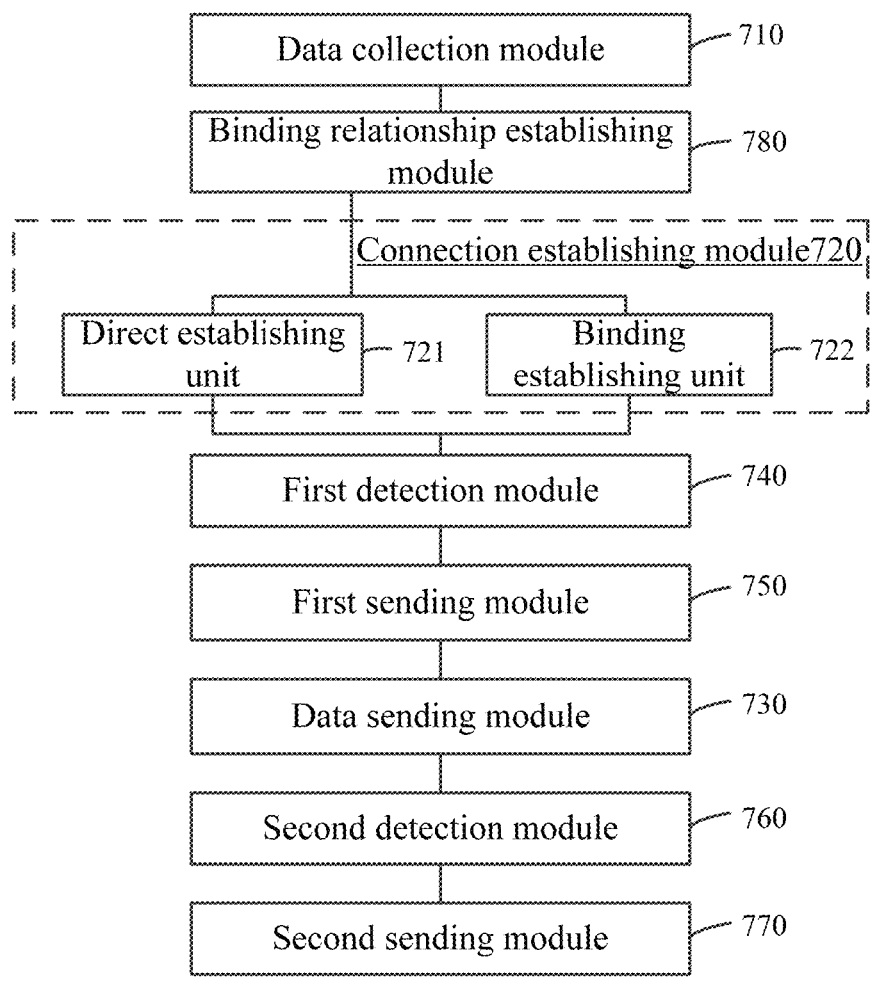
FIG. 7 is a block diagram of an apparatus for displaying health data according to embodiments of the disclosure.

Referring to FIG. 7, it shows an example block diagram of an apparatus for displaying health data according to a further exemplary embodiment. The apparatus for displaying health data may be implemented as a part or all of the wearable device 120 in the implementation environment shown in FIG. 1 through software, hardware, or combination thereof. The file execution apparatus may comprise: a data collection module 710, a connection establishing module 720 and a data sending module 730.

The data collection module 710 is configured to collect health data of a user.

The connection establishing module 720 is configured to establish a wireless connection with a home media playing device.

The data sending module 730 is configured to send the health data to the home media playing device through the wireless connection, the home media playing device being used to receive and display the health data.

In some embodiments, the connection establishing module 720 may include one of: a direct establishing unit 721 and a binding establishing unit 722. The direct establishing unit 721 is configured to establish the wireless connection with the home media playing device directly. The binding establishing unit 722 is configured to establish the wireless connection with the home media playing device by a bound mobile terminal.

The apparatus may further include: a first detection module 740 and a first sending module 750. The first detection module 740 is configured to detect whether a turn-on trigger condition exists. The first sending module 750 is configured to send a turn-on instruction to the home media playing device if the turn-on trigger condition exists, where the home media playing device may be used to enter an operating state after receiving the turn-on instruction. The turn-on trigger condition may include: a first designated time is reached, or a collected body gesture conforms to a first gesture, or a distance between the wearable device and the home media playing device is less than a preset distance.

The apparatus may further include: a second detection module 760 configured to detect whether a turn-off trigger condition exists; and a second sending module 770 configured to send a turn-off instruction to the home media playing device if the turn-off trigger condition exists, the home media playing device is used to enter a sleep state or a shutdown state after receiving the turn-off instruction. The turn-off trigger condition may include at least one of the following conditions: a second designated time is reached, or a collected body gesture conforms to a second gesture, or a distance between the wearable device and the home media playing device is greater than a preset distance.

The apparatus may further include: a binding relationship establishing module 780 configured to establish a binding relationship with the home media playing device in advance.

The binding relationship establishing module 780 may be configured to send a wearable device identification and a user account to a server, the server is programmed to establish the binding relationship of the wearable device with the user account and the home media playing device corresponding to the user account according to the identification of the wearable device; or the binding relationship establishing module 780 is configured to send the identification of the wearable device and the user account to the server by the bound mobile terminal, the server is programmed to establish the binding relationship of the wearable device with the user account and the home media playing device corresponding to the user account according to the identification of the wearable device; or the binding relationship establishing module 780 is configured to send the identification of the wearable device and the user account to the server by the home media playing device, the server is programmed to establish the binding relationship of the wearable device with the user account and the home media playing device corresponding to the user account according to the identification of the wearable device.

In summary, in the apparatus for displaying health data provided by the embodiments of the present disclosure, by collecting health data of the user, establishing the wireless connection with the home media playing device, sending the health data to the home media playing device through the wireless connection, and displaying the health data by the home media playing device, the problems in the related that the health data in a wearable device is displayed only after the wearable device and a computer are connected using a data cable, causing that the operation process is complicated and the utilization efficiency is lower are solved. Therefore, the user operation is simplified, and the utilization efficiency is improved.

In the apparatus for displaying health data provided by the embodiments of the present disclosure, by establishing the wireless connection with the home media playing device directly, or by establishing the wireless connection with the home media playing device through the bound mobile terminal, the manner of establishing the wireless connection is enriched.

The apparatus for displaying health data provided by the embodiments of the present disclosure, by sending the turn-on instruction to the home media playing device after the turn-on trigger condition is detected, so that the home media playing device enters the operating state according to the turn-on instruction, so as to receive the health data sent by the wearable device, therefore, it is ensured that the home media playing device may accurately receive the health data; further, by sending the turn-off instruction to the home media playing device after the turn-off trigger condition is detected, so that the home media playing device enters the sleep or the shutdown state according to the turn-off instruction, therefore, the security of health data of the user is ensured.

The apparatus for displaying health data provided by the embodiments of the present disclosure, by sending the turn-on instruction to the home media playing device when detecting that the first designated time is reached, or detecting that the collected body gesture conforms to the first gesture, or detecting that the distance between the wearable device and the home media playing device is less than the preset distance, and by sending the turn-off instruction to the home media playing device when detecting that the second designated time is reached, or detecting that the collected body gesture conforms to the second gesture, or detecting that the distance between the wearable device and the home media playing device is greater than the preset distance; therefore, a trigger mode of the trigger open condition and the closed condition is enriched.

The apparatus for displaying health data provided by the embodiments of the present disclosure, by establishing the binding relationship with the home media playing device in advance, therefore, it is ensured that the method for displaying the healthy data may be carried out smoothly; further, by sending the identification of the wearable device and the user account to the server, or sending the identification of the wearable device and the user account to the server by the bound mobile terminal, or sending the identification of the wearable device and the user account to the server by the home media playing device, the binding to the wearable device, the home media playing device and the user account may be made by the server, therefore, the variety of the binding way is ensured.

Figure 8:
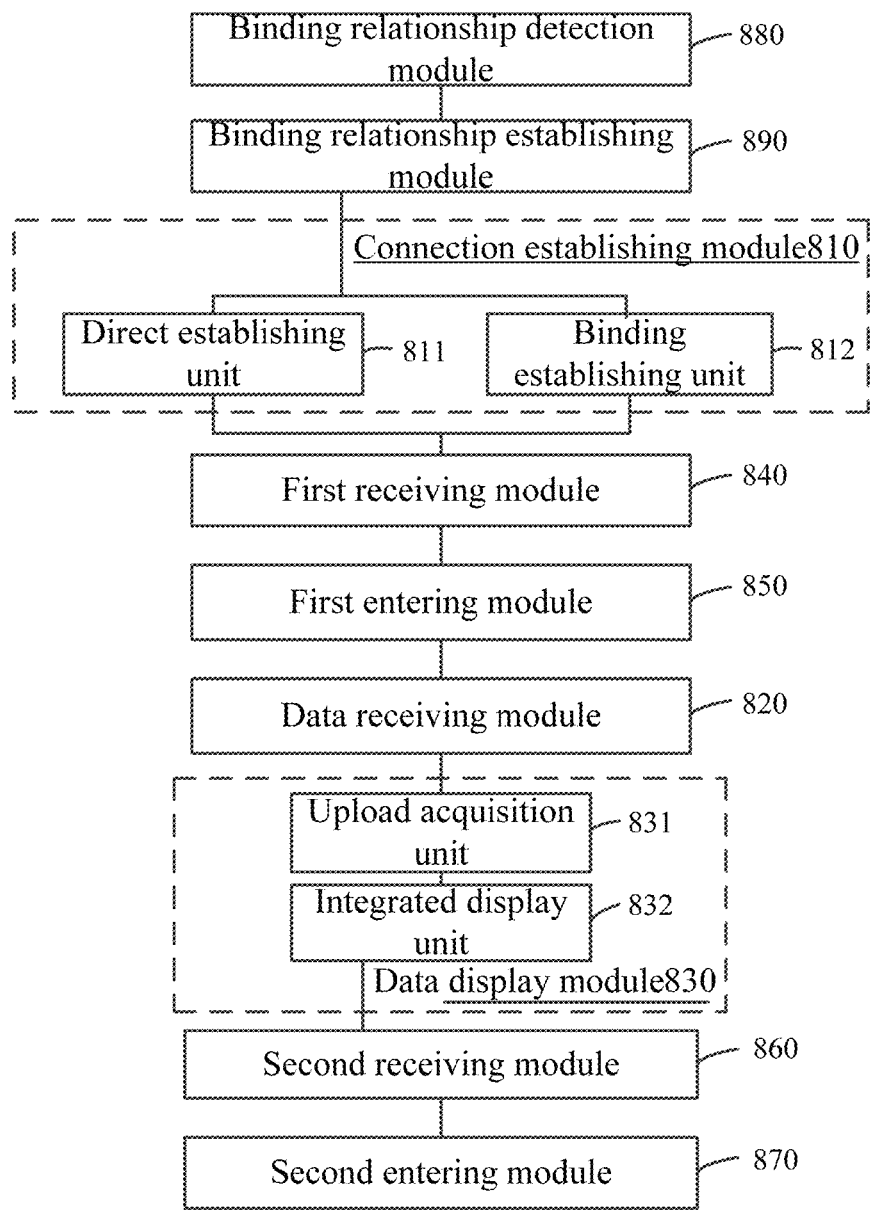
FIG. 8 is a block diagram of an apparatus for displaying health data according to a further exemplary embodiment.

Referring to FIG. 8, it shows a block diagram of an apparatus for displaying health data according to a further exemplary embodiment. The apparatus for displaying health data may be implemented as a part or all of the home media playing device 140 in the implementation environment shown in FIG. 1 through software, hardware, or combination thereof. The file execution apparatus may comprise: a connection establishing module 810, a data receiving module 820 and a data display module 830.

The connection establishing module 810 is configured to establish a wireless connection with the wearable device.

The data receiving module 820 is configured to receive health data of a user sent by the wearable device through the wireless connection.

The data display module 830 is configured to display the health data.

In some embodiments, the connection establishing module 810 may include:

a direct establishing unit 811 configured to establish the wireless connection with the wearable device directly; or a binding establishing unit 812 configured to establish the wireless connection with the wearable device via a mobile terminal bound with the wearable device.

The apparatus may further include: a first receiving module 840 configured to receive a turn-on instruction sent by the wearable device; and a first entering module 850 configured to enter an operating state according to the turn-on instruction.

The apparatus may further include: a second receiving module 860 configured to receive a turn-off instruction sent by the wearable device; and a second entering module 870 configured to enter a sleep state or a shutdown state according to the turn-off instruction.

The data display module 830 may include: an upload acquisition unit 831 configured to upload the health data to a server, and acquiring historical health data from the server; and an integrated display unit 832 configured to integrate and display the acquired historical health data and the health data.

The apparatus may further include: a binding relationship detection module 880 configured to detect whether it is a binding relationship with the wearable device; and trigger the connection establishing module to establish the wireless connection with the wearable device if it is the binding relationship with the wearable device.

The apparatus may further include: a binding relationship establishing module 890 configured to establish the binding relationship with the wearable device in advance.

The binding relationship establishing module 890 may be configured to send an identification of the home media playing device and a user account to a server, the server is used to establish the binding relationship of the home media playing device with the user account and the wearable device corresponding to the user account according to the identification of the home media playing device.

In summary, the apparatus for displaying health data provided by the embodiments of the present disclosure, by establishing the wireless connection with the wearable device, receiving health data of the user sent by the wearable device through the wireless connection; and displaying the health data, the problems in the related that the health data in a wearable device is displayed only after the wearable device and a computer are connected using a data cable, the operation process is complicated and the utilization efficiency is lower are solved. Therefore, the user operation is simplified, and the utilization efficiency is improved.

The apparatus for displaying health data provided by the embodiments of the present disclosure, by establishing the wireless connection with the home media playing device directly, or by establishing the wireless connection with the home media playing device through the bound mobile terminal, therefore, the way of establishing the wireless connection is enriched.

The apparatus for displaying health data provided by the embodiments of the present disclosure, by receiving the turn-on instruction sent by the wearable device, entering the operating state according to the turn-on instruction, thus receiving the health data sent by the wearable device; therefore, it is ensured that the health data may be received accurately; further, by receiving the turn-off instruction sent by the wearable device, entering the sleep or the shutdown state according to the turn-off instruction, therefore, the security of health data of the user is ensured.

The apparatus for displaying health data provided by the embodiments of the present disclosure, by uploading the health data to the server after receiving the health data, and acquiring the historical health data from the server, thus integrating the health data and the historical health data, so that the user may understand their own health state more clearly, and the integrity of the user's data saved by the server is ensured.

The apparatus for displaying health data provided by the embodiments of the present disclosure, by establishing the binding relationship with the wearable device in advance, it is ensured that the above method for displaying the health data may be carried out smoothly.

With respect to the device in the above embodiments, specific operations performed by each module have been described in detail in the embodiments of related method, and detailed description will not be repeated here.

Figure 9:
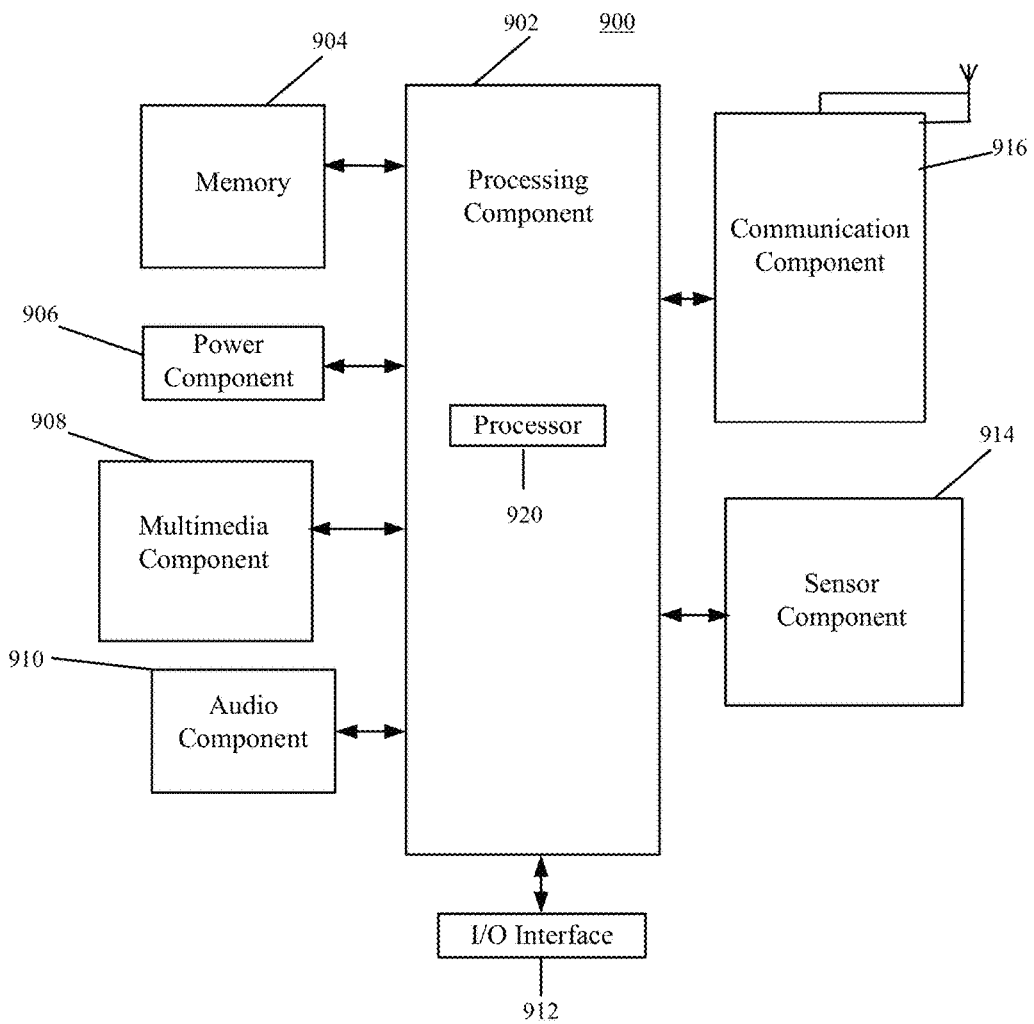
FIG. 9 is a block diagram of an apparatus for displaying health data according to embodiments of the disclosure.

FIG. 9 is a block diagram showing a device 900 for displaying health data according to an exemplary embodiment. For example, the device 900 may be a home media playing device, such as a smart TV, a projector, LCD (Liquid Crystal Display), a computer and the like.

Referring to FIG. 9, the device 900 may include one or more of the following components: a processing component 902, a memory 904, a power component 906, a multimedia component 908, an audio component 910, an input/output (I/O) interface 912, a sensor component 914, and a communication component 916.

The processing component 902 usually controls overall operations of the device 900, such as the operations associated with display, telephone calls, data communications, camera operations, and recording operations. The processing component 902 may include one or more processors 920 to execute instructions to perform all or part of the steps in the above methods. Moreover, the processing component 902 may include one or more modules which facilitate the interaction between the processing component 902 and other components. For instance, the processing component 902 may include a multimedia module to facilitate the interaction between the multimedia component 908 and the processing component 902.

The memory 904 is configured to store various types of data to support the operation of the device 900. Examples of such data include instructions for any application or method operated on the device 900, contact data, phonebook data, messages, pictures, videos, etc. The memory 904 may be implemented using any type of volatile or non-volatile memory device or combination thereof, such as a static random access memory (SRAM), an electrically erasable programmable read-only memory (EEPROM), an erasable programmable read-only memory (EPROM), a programmable read-only memory (PROM), a read-only memory (ROM), a magnetic memory, a flash memory, a magnetic or optical disk.

The power component 906 provides power to various components of the device 900. The power component 906 may include a power management system, one or more power sources, and other components associated with the generation, management, and distribution of power in the device 900.

The multimedia component 908 includes a screen providing an output interface between the device 900 and the user. In some embodiments, the screen may include a liquid crystal display (LCD) and a touch panel (TP). If the screen includes the touch panel, the screen may be implemented as a touch screen to receive input signals from the user. The touch panel includes one or more touch sensors to sense touches, slips, and gestures on the touch panel. The touch sensors may not only sense a boundary of a touch or slip action, but also sense a period of time and a pressure associated with the touch or slip action. In some embodiments, the multimedia component 908 includes a front camera and/or a rear camera. The front camera and/or the rear camera may receive an external multimedia datum while the device 900 is in an operation mode, such as a photographing mode or a video mode. Each of the front camera and the rear camera may be a fixed optical lens system or have focus and optical zoom capability.

The audio component 910 is configured to output and/or input audio signals. For example, the audio component 910 includes a microphone (MIC) configured to receive an external audio signal when the device 900 is in an operation mode, such as a call mode, a recording mode, and a voice identification mode. The received audio signal may be further stored in the memory 904 or transmitted via the communication component 916. In some embodiments, the audio component 910 may further include a speaker to output audio signals.

The I/O interface 912 provides an interface between the processing component 902 and peripheral interface modules, such as a keyboard, a click wheel, a button, and the like. The button may include, but not limited to, a home button, a volume button, a starting button, and a locking button.

The sensor component 914 includes one or more sensors to provide state assessments of various aspects of the device 900. For instance, the sensor component 914 may detect an open/shutdown state of the device 900, relative positioning of components, e.g., the display and the keyboard, of the device 900, a change in position of the device 900 or a component of the device 900, a presence or absence of user contact with the device 900, an orientation or an acceleration/deceleration of the device 900, and a change in temperature of the device 900. The sensor component 914 may include a proximity sensor configured to detect the presence of nearby objects without any physical contact. The sensor component 914 may also include a light sensor, such as a CMOS or CCD image sensor, for use in imaging applications. In some embodiments, the sensor component 914 may also include an accelerometer sensor, a gyroscope sensor, a magnetic sensor, a pressure sensor, or a temperature sensor.

The communication component 916 is configured to facilitate communication, wired or wirelessly, between the device 900 and other devices. The device 900 can access a wireless network based on a communication standard, such as Wi-Fi, 2G, or 3G, or a combination thereof. In one exemplary embodiment, the communication component 916 receives a broadcast signal or broadcast associated information from an external broadcast management system via a broadcast channel. In some embodiments, the communication component 916 may further include a near field communication (NFC) module to facilitate short-range communications. For example, the NFC module may be implemented based on a radio frequency identification (RFID) technology, an infrared data association (IrDA) technology, an ultra-wideband (UWB) technology, a Bluetooth (BT) technology, and other technologies.

In exemplary embodiments, the device 900 may be implemented with one or more application specific integrated circuits (ASICs), digital signal processors (DSPs), digital signal processing devices (DSPDs), programmable logic devices (PLDs), field programmable gate arrays (FPGAs), controllers, micro-controllers, microprocessors, or other electronic components, for performing the above method.

In exemplary embodiments, there is also provided a non-transitory computer readable storage medium including instructions, such as included in the memory 904, executable by the processor 920 in the device 900, for performing the above method. For example, the non-transitory computer-readable storage medium may be a ROM, a random access memory (RAM), a CD-ROM, a magnetic tape, a floppy disc, an optical data storage device, and the like.

A non-transitory computer readable storage medium, when instructions in the storage medium are executed by the processor of a device 900, the device 900 may execute a method for displaying health data.

Figure 10:
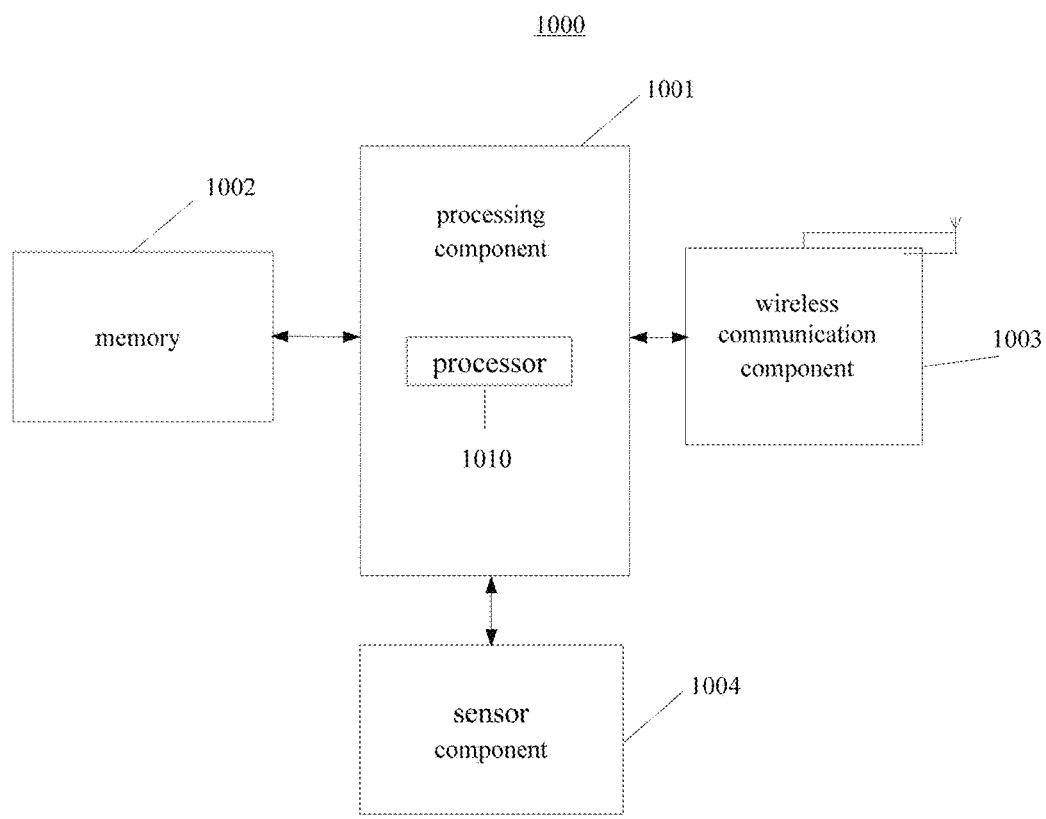
FIG. 10 is a block diagram of an apparatus for displaying health data according to embodiments of the disclosure.

FIG. 10 is a block diagram showing a device 1000 for displaying health data according to an exemplary embodiment. For example, the device 1000 may be a wearable device, such as a smart bracelet, a smart watch and the like.

Referring to FIG. 10, the device 1000 may include one or more of the following components: a processing component 1001, a memory 1002, a wireless communication component 1003, and a sensor component 1004.

The processing component 1001 usually controls overall operations of the device 1000, such as the operations associated with collecting health data of a user, sending the health data, uploading the health data to a server and the like. The processing component 1001 may include one or more processors 1010 to execute instructions to perform all or part of the steps in the above methods. Moreover, the processing component 1001 may include one or more modules which facilitate the interaction between the processing component 1001 and other components. For instance, the processing component 1001 may include a wireless communication module to facilitate the interaction between the wireless communication component 1003 and the processing component 1001.

The memory 1002 is configured to store various types of data to support the operation of the device 1000. Examples of such data include instructions for any application or method operated on the device 1000, health data, time data, position data, gestures, etc. The memory 1002 may be implemented using any type of volatile or non-volatile memory device or combination thereof, such as a static random access memory (SRAM), an electrically erasable programmable read-only memory (EEPROM), an erasable programmable read-only memory (EPROM), a programmable read-only memory (PROM), a read-only memory (ROM), a magnetic memory, a flash memory, a magnetic or optical disk.

The wireless communication component 1003 is configured to facilitate communication, wired or wirelessly, between the device 1000 and other devices. The device 1000 can access a wireless network based on a communication standard including but not limited to: Wi-Fi, Bluetooth, and infrared. In one exemplary embodiment, the wireless communication component 1003 sends the health data collected by the wearable device to the home media playing device, so that the home media playing device may display the health data. In some embodiments, the wireless communication component 1003 may further includes a near field communication (NFC) module to facilitate short-range communications. For example, the NFC module may be implemented based on a radio frequency identification (RFID) technology, an infrared data association (IrDA) technology, an ultra-wideband (UWB) technology, a Bluetooth (BT) technology, and other technologies.

The sensor component 1004 includes one or more sensors to provide state assessments of various aspects of the device 1000 and collect health data of the user. For instance, the sensor component 1004 may detect an open/shutdown state of the device 1000, relative positioning of components, a change in position of the device 1000 or a component of the device 1000, a presence or absence of user contact with the device 1000, an orientation or an acceleration/deceleration of the device 1000, and a change in temperature of the device 1000. The sensor component 1004 may include a proximity sensor configured to detect the presence of nearby objects without any physical contact. The sensor component 1004 may also include a health data sensor, for collecting health data of the user. The sensor component 1004 may also include a gesture sensor, for collecting the user's gestures. In some embodiments, the sensor component 1004 may also include an accelerometer sensor, a gyroscope sensor, a magnetic sensor, a pressure sensor, a temperature sensor, a pedometer, a heart rate sensor, an electronic compass sensor and the like.

In exemplary embodiments, the device 1000 may be implemented with one or more application specific integrated circuits (ASICs), digital signal processors (DSPs), digital signal processing devices (DSPDs), programmable logic devices (PLDs), field programmable gate arrays (FPGAs), controllers, micro-controllers, microprocessors, or other electronic components, for performing the above method.

In exemplary embodiments, there is also provided a non-transitory computer readable storage medium including instructions, such as included in the memory 1002, executable by the processor 1010 in the device 1000, for performing the above method. For example, the non-transitory computer-readable storage medium may be a ROM, a random access memory (RAM), a CD-ROM, a magnetic tape, a floppy disc, an optical data storage device, and the like.

A non-transitory computer readable storage medium, when instructions in the storage medium are executed by the processor of a device 1000, the device 1000 may execute a method for displaying health data.

After considering this description and carrying out the embodiments disclosed herein, those skilled in the art may easily anticipate other implementation aspects of the present disclosure. The present disclosure is meant to cover any variations, usage or adaptive change of these embodiments, and these variations, usage or adaptive change follow general concept of the present disclosure and include the common knowledge or the customary technical means in the technical field that is not disclosed in the present disclosure. The description and embodiments are only exemplary, and the real range and spirit of the present disclosure are defined by the following claims.

It should be understood that the present disclosure is not limited to precise structures that are described above and shown in the accompanying drawings, and may be modified and changed without departing from the range of the present disclosure. The scope of the present disclosure is only defined by the appended claims.

What is claimed is:

1. A method for displaying health data, comprising:
   collecting, by a wearable device, health data of a user;
   establishing, by the wearable device, a wireless connection with a home media playing device having a display screen;
   sending, by the wearable device, a turn-on instruction or a turn-off instruction to the home media playing device according to a collected body gesture involving the wearable device; and
   sending, by the wearable device, the health data to the home media playing device through the wireless connection for displaying the health data in a preset time period on the display screen according to a number of consecutive gestures involving the wearable device, wherein the number of consecutive gestures determines a duration of the preset time period.

2. The method according to claim 1, wherein establishing the wireless connection with the home media playing device comprises one of the following:
   establishing the wireless connection with the home media playing device directly; and
   establishing the wireless connection with the home media playing device by a bound mobile terminal.

3. The method according to claim 1, wherein, the method further comprises:
   detecting, by the wearable device, whether a turn-on trigger condition exists; and
   sending the turn-on instruction to the home media playing device if the turn-on trigger condition exists, whereby the home media playing device enters an operating state after receiving the turn-on instruction,
   wherein the turn-on trigger condition occurs when: a first designated time is reached, the collected body gesture conforms to a first gesture, or a distance between the wearable device and the home media playing device is less than a preset distance.

4. The method according to claim 1, wherein, the method further comprises:
   detecting, by the wearable device, whether a turn-off trigger condition exists; and
   sending, by the wearable device, the turn-off instruction to the home media playing device if the turn-off trigger condition exists, whereby the home media playing device enters a sleep state or a shutdown state after receiving the turn-off instruction,
   wherein the turn-off trigger condition occurs when: a second designated time is reached, the collected body gesture conforms to a second gesture, or a distance between the wearable device and the home media playing device is greater than a preset distance.

5. The method according to claim 1, wherein the method further comprises:
   establishing a binding relationship with the home media playing device in advance.

6. The method according to claim 5, wherein establishing the binding relationship with the home media playing device in advance comprises at least one of the following:
   sending a wearable device identification and a user account to a server, whereby the server establishes the binding relationship of the wearable device with the user account and the home media playing device corresponding to the user account according to the identification of the wearable device;
   sending the identification of the wearable device and the user account to the server by the bound mobile terminal, whereby the server establishes the binding relationship of the wearable device with the user account and the home media playing device corresponding to the user account according to the identification of the wearable device; and
   sending the identification of the wearable device and the user account to the server by the home media playing device, whereby the server establishes the binding relationship of the wearable device with the user account and the home media playing device corresponding to the user account according to the identification of the wearable device.

7. A method for displaying health data, comprising:
   establishing, by a home media playing device comprising a display screen, a wireless connection with a wearable device;

receiving, by the home media playing device, health data of a user sent by the wearable device through the wireless connection;

displaying, by the home media playing device, the health data in a preset time period on the display screen according to a number of consecutive gestures involving the wearable device, wherein the number of consecutive gestures determines a duration of the preset time period; and entering, by the home media playing device, a sleep state when a distance between the wearable device and the home media playing device is less than a preset distance.

8. The method according to claim 7, wherein establishing the wireless connection with the wearable device comprises one of the following:

establishing the wireless connection with the wearable device directly; and establishing the wireless connection with the wearable device via a mobile terminal bound with the wearable device.

9. The method according to claim 7, further comprising:

receiving, by the home media playing device, a turn-on instruction sent by the wearable device; and entering, by the home media playing device, an operating state according to the turn-on instruction.

10. The method according to claim 7, further comprising:

receiving, by the home media playing device, a turn-off instruction sent by the wearable device when the wearable device detects that a second designated time is reached or a collected body gesture conforms to a second gesture; and entering, by the home media playing device, a shutdown state according to the turn-off instruction.

11. The method according to claim 7, wherein displaying the health data comprises:

uploading the health data to a server, and acquiring historical health data from the server; and integrating and displaying the acquired historical health data and the health data.

12. The method according to claim 7, further comprising:

detecting whether it is a binding relationship with the wearable device; and performing the step of the establishing the wireless connection with the wearable device if it is the binding relationship with the wearable device.

13. The method according to claim 12, further comprising:

establishing the binding relationship with the wearable device in advance.

14. The method according to claim 13, wherein, the establishing the binding relationship with the wearable device in advance comprises:

sending an identification of the home media playing device and a user account to a server, whereby the server establishes the binding relationship of the home media playing device with the user account and the wearable device corresponding to the user account according to the identification of the home media playing device.

15. A wearable device, comprising:

a processor; and a memory for storing instructions executable by the processor;

wherein the processor is configured to:

collect health data by one or more hardware sensors in the wearable device;

establish a wireless connection with a home media playing device including a display screen;

send a turn-on instruction or a turn-off instruction to the home media playing device according to a collected body gesture involving the wearable device; and send the health data to the home media playing device through the wireless connection for displaying the health data in a preset time period on the display screen according to a number of consecutive gestures involving the wearable device, wherein the number of consecutive gestures determines a duration of the preset time period.

16. The wearable device according to claim 15, wherein the wearable device establishes the wireless connection with the home media playing device through one of the following:

establishing the wireless connection with the home media playing device directly; and establishing the wireless connection with the home media playing device by a bound mobile terminal.

17. The wearable device according to claim 15, wherein the processor is further configured to:

detect whether a turn-on trigger condition exists; and send the turn-on instruction to the home media playing device if the turn-on trigger condition exists, whereby the home media playing device enters an operating state after receiving the turn-on instruction;

wherein the turn-on trigger condition occurs when: a first designated time is reached, the collected body gesture conforms to a first gesture, or a distance between the wearable device and the home media playing device is less than a preset distance.

18. The wearable device according to claim 15, wherein the processor is further configured to:

detect whether a turn-off trigger condition exists; and send the turn-off instruction to the home media playing device if the turn-off trigger condition exists, whereby the home media playing device enters a sleep state or a shutdown state after receiving the turn-off instruction;

wherein the turn-off trigger condition occurs when: a second designated time is reached, the collected body gesture conforms to a second gesture, or a distance between the wearable device and the home media playing device is greater than a preset distance.

19. The wearable device according to claim 15, wherein the processor is further configured to:

establish a binding relationship with the home media playing device in advance.

20. The wearable device according to claim 19, wherein establishing the binding relationship with the home media playing device in advance comprises at least one of the following:

sending a wearable device identification and a user account to a server, whereby the server establishes the binding relationship of the wearable device with the user account and the home media playing device corresponding to the user account according to the identification of the wearable device;

sending the identification of the wearable device and the user account to the server by the bound mobile terminal, whereby the server establishes the binding relationship of the wearable device with the user account and the home media playing device corresponding to the user account according to the identification of the wearable device; and sending the identification of the wearable device and the user account to the server by the home media playing device, whereby the server establishes the binding relationship of the wearable device with the user account and the home media playing device corresponding to the user account according to the identification of the wearable device.

* * * * *